US00PP23876P3

(12) United States Plant Patent
Jensen

(10) Patent No.: US PP23,876 P3
(45) Date of Patent: Sep. 3, 2013

(54) ***CAMPANULA* PLANT NAMED 'B.09.01'**

(50) Latin Name: ***Campanula portenschlagiana* Schult.**
Varietal Denomination: B.09.01

(75) Inventor: Gert Kim Jensen, Marslev (DK)

(73) Assignee: Rosa-Danica A/S, Marslev (DK)

( * ) Notice: Subject to any disclaimer, the term of this patent is extended or adjusted under 35 U.S.C. 154(b) by 113 days.

(21) Appl. No.: 13/067,310

(22) Filed: May 24, 2011

(65) Prior Publication Data

US 2012/0304352 P1 Nov. 29, 2012

(51) Int. Cl.
*A01H 5/00* (2006.01)

(52) U.S. Cl.
USPC ..... Plt./414

(58) Field of Classification Search
USPC ..... Plt./414
See application file for complete search history.

(56) References Cited

PUBLICATIONS

Printout of application information from Community Plant Variety Office (CPVO) website for corresponding CPVO application No. 2011/0541 filed Feb. 28, 2011 (1 page). (http://www.cpvoextranet.cpvo.europa.eu).

*Primary Examiner* — June Hwu
(74) *Attorney, Agent, or Firm* — Foley & Lardner LLP

(57) ABSTRACT

A new and distinct cultivar of *Campanula* plant named B.09.01, characterized by its compact upright plant habit; dense and bushy plant form; vigorous growth habit; and large, upright, violet-colored flowers.

3 Drawing Sheets

Latin name of the genus and species claimed: *Campanula portenschlagiana* Schult.

Variety denomination: 'B.09.01'.

BACKGROUND OF THE INVENTION

The present Invention relates to a new and distinct cultivar of *Campanula* plant, botanically known as *Campanula portenschlagiana* Schult., common name Dalmatian Bellflower and hereinafter referred to by the code 'B.09.01'.

The new *Campanula* is a product of a planned breeding program conducted by Gert Kim Jensen, in Marslev, Denmark. The new *Campanula* originated from a cross made in 2009 by the Inventor between a proprietary selection of *Campanula portenschlagiana* Schult, (unpatented, breeder reference 08.98.05) as the female parent, and the cultivar 'CBO-1'('Blue Ocean') (patented, U.S. Plant Pat. No. 21,733) as the male parent. The Inventor selected the new *Campanula* cultivar from the progeny of the above crossing in 2009 on the basis of its compact, upright growth, with low need for retardation and fungicides and distinctive flowering.

Asexual reproduction of the new *Campanula* cultivar by terminal vegetative cuttings was first performed in 2009 in Marslev, Denmark, and has demonstrated that the combination of characteristics as herein disclosed for the new cultivar are firmly fixed and retained through successive generations of asexual reproduction. The new cultivar reproduces true to type.

SUMMARY OF THE INVENTION

Plants of the *Campanula* cultivar 'B.09.01' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'B.09.01'. These characteristics in combination distinguish 'B.09.01' as a new and distinct cultivar:

1. Violet, single-bell flowers;
2. Higher numbers of flowers per plant;
3. Dense and bushy plant form, mainly due to more upright stems;
4. Upright plant habit;
5. Less need for growth retardant;

When plants of the cultivar 'B.09.01' are compared to plants of the parent cultivars '08.98.05' (female) and 'CBO-1' (male), the varieties differ in the following characteristics:

1. Plants of the new *Campanula* 'B.09.01' have more upright growth than plants of either parent cultivar;
2. Plants of the new *Campanula* 'B.09.01' have no requirement for treatment by growth retardant, as do both parent cultivars.

Plants of the cultivar 'B.09.01' can be compared to plants of the *Campanula portenschlagiana* Schult. cultivar 'PKMp01' ('Get Mee') (patented, U.S. Plant Pat. No. 17,205). However, in side-by-side comparisons conducted by the Inventor in Marslev, Denmark, plants of the cultivar 'B.09.01' and the cultivar 'GetMee' differ in the following characteristics, it must however be mentioned that the new cultivar plant examined has not been treated with growth retardant.

1. Plants of the new *Campanula* 'B.09.01' have deep violet, single bell, upright flowers compared to the blue flowers of 'GetMee';
2. Plants of the new *Campanula* 'B.09.01' have more upright growth than plants of the cultivar 'GetMee';
3. Plants of the new *Campanula* 'B.09.01' do not need growth retardant treatment;
4. Plants of the new *Campanula* 'B.09.01' have more flowers per plant than the plants of the cultivar 'GetMee'; and 5. Plants of the new *Campanula* 'B.09.01' appear to be less susceptible to grey mold.

BRIEF DESCRIPTION OF THE PHOTOGRAPHS

The patent or application file contains at least one drawing executed in color. Copies of this patent or patent application publication with color drawing(s) will be provided by the Office upon request and payment of the necessary fee.

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which more accurately describe the actual colors of the new *Campanula.*

DETAILED BOTANICAL DESCRIPTION

Figure 1:
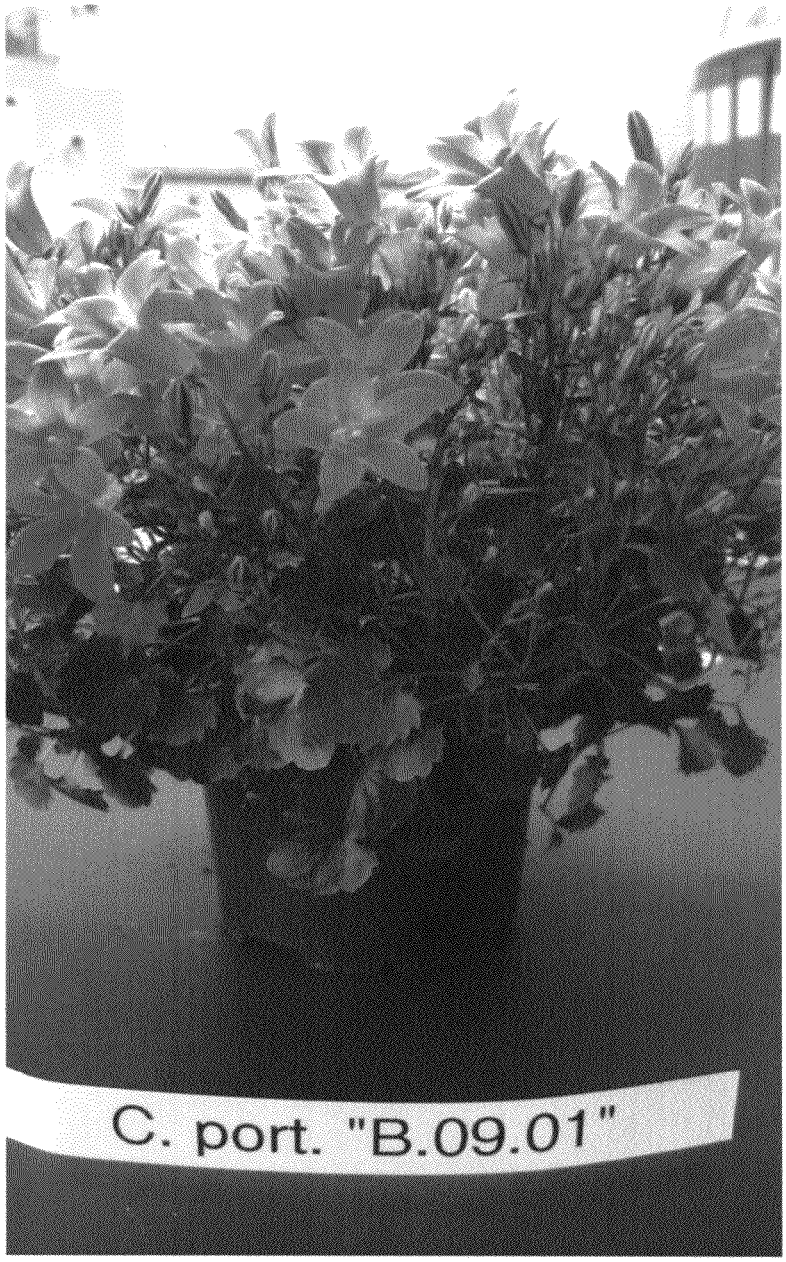
FIG. 1 is a side perspective view of a typical flowering plant of 'B.09.01', at approximately 18 weeks old.
Figure 2:
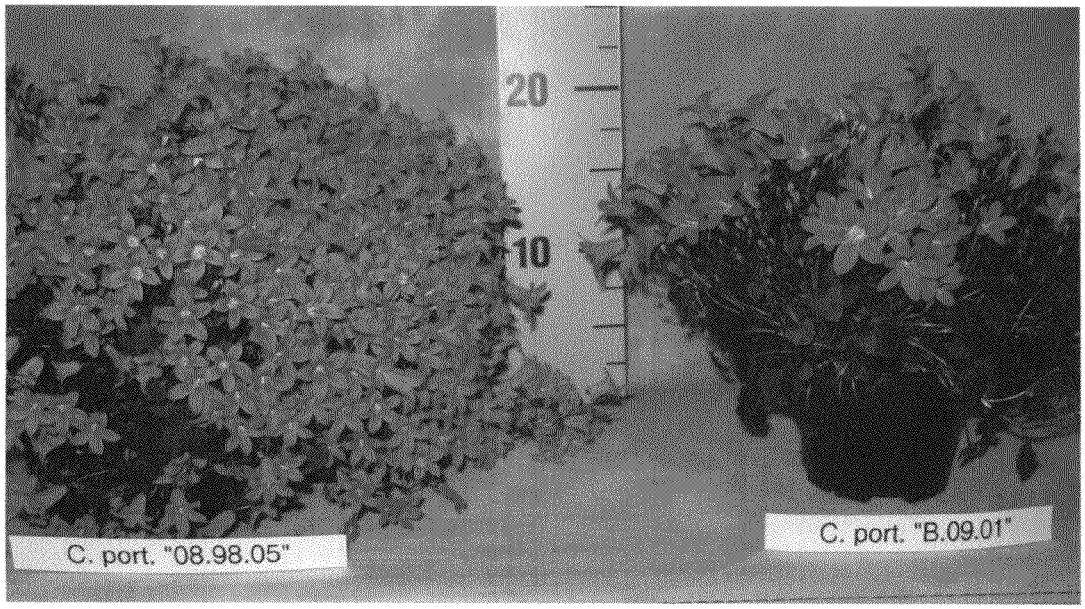
FIG. 2 is a side perspective view of a typical flowering plant of 'B.09.01' as compared to a typical flowering plant of '08.98.05', both approximately 18 weeks old and grown in 11 cm pots.
Figure 3:
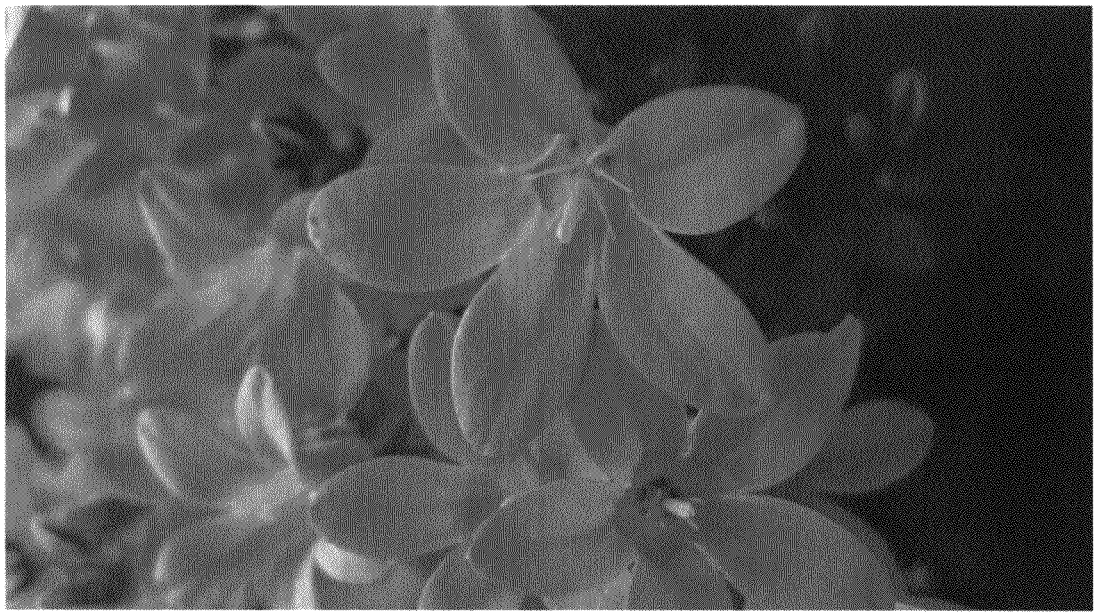
FIG. 3 is a close-up view of typical single flowers of 'B.09.01'.

In the following description, color references are made to The Royal Horticultural Society Colour Chart, 4$^{th}$ edition, where general terms of ordinary dictionary significance are used. Plants were grown under greenhouse conditions as stated in the detailed description sheet. Plants used for this description were grown for about 14 weeks after cutting Botanical classification:

*Campanula portenschlagiana Schuh.*—

*Variety denomination.*—'B.09.01'.

Parentage:

*Female parent.*—Unnamed proprietary selection of *Campanula portenschlagiana* Schult, (unpatented, breeder reference '08.98.05').

*Male parent.*—*Campanula portenschlagiana* Schult, variety 'CBO-1'('Blue Ocean') (patented, U.S. Plant Pat. No. 21,733).

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Perennial plant with ascending to upright globular plant habit. Campanulate flowers in racemes. Freely branching with lateral branches forming at every node; dense and bushy. Freely branching, somewhat brittle stems.

*Crop time.*—After rooting, about 14 weeks are required to produce finished flowering plants in 11 cm pots.

*Plant height* (*soil level to top of plant plane*).—About 14 cm.

*Plant diameter.*—20 cm.

*Vigor.*—Vigorous growth rate.

Foliage:

*Leaves.*—Alternate, single, dentate, palmate (actinodromous).

*Venation.*—Not very conspicuous.

*Basal leaves.*—Length: 25-27 mm. Width: About 25 mm. Shape: Cordate. Apex: acuminate. Base: Cordate. Margin: broadly dentate. Texture: smooth, glabrous, dull. Few short stiff hairs on abaxial side and along veins and margin. Color: Young foliage, upper and lower surfaces: RHS 136B, green. Mature foliage, upper and lower surfaces: RHS 137B, green. Venation: RHS 137D. Petioles on basal leaves: 5 cm. Petioles on apical leaves: 5 mm.

Flowers:

*Arrangement and shape.*—Single flowers in racemes; Violet campanulate flowers with small star shaped calyx.

*Natural flowering season.*—Continuous throughout the spring and summer in Denmark. Season can be extended by long day treatments. 7 weeks (14 hours) are needed for flower induction under greenhouse conditions.

*Flower longevity on the plant.*—Longevity (9 to 14 days) of individual flowers is highly dependent on temperature and light conditions. Flowers persistent.

*Inflorescence length.*—About 11 cm.

*Inflorescence height.*—About 10-12 cm.

*Inflorescence width* (*diameter*).—6-8 cm.

*Average number of flowers per raceme.*—17-22.

*Flower buds.*—Color: RHS 143C, green, a slight tinge of RHS 85D on upper parts of opening corolla. Length: up to 140 mm. Width: 4 mm wide before anthesis.

*Aspect.*—Upright.

*Length.*—About 17 mm.

*Diameter.*—About 28 mm.

*Shape.*—Broadly arrow shaped.

*Acuminate petal lobes.*—Length: 11 mm. Width: 7 mm wide at basis.

*Corolla color.*—Upper and lower surfaces, RHS N87B (¼ bottom of bell: RHS N87D). Maturing to RHS N87C.

*Pistil and stigma.*—Conspicuous; tripartite; same color as petals.

*Peduncle.*—Strength: Moderately strong. Length: About 17 mm. Diameter: About 1 mm. Color: RHS 144B yellow-green.

*Sepal.*—Length: 3 mm. Width: 1 mm. Shape: Arrow-shaped. Texture: Shiny, glabrous. Color: Immature, upper and under side: RHS 144B. Mature, upper and under side: RHS 138A.

*Pedicel.*—Average Length: 13-15 mm. Texture: Smooth and shiny. Color: Between RHS 145A and RHS 145B.

*Stamen.*—Number: 5, fused until pollen has shed. Size: 1 mm. Color: RHS 158B, Yellow-White. Pollen Amount: Average. Pollen Color: RHS 158B, Yellow-White.

*Pistil.*—Number: 1.

*Seed.*—Length: About 1 mm. Diameter: About 0.3 mm.

Weather tolerance: Plants of the claimed variety have not been tested for tolerance to drought, rain and wind, low temperature.

Disease resistance: Plants of the claimed variety have shown good resistance to grey mold.

What is claimed is:

1. A new and distinct cultivar of *Campanula* plant named 'B.09.01', as illustrated and described herein.

* * * * *